US012603191B2

(12) United States Patent
Mervin

(10) Patent No.: US 12,603,191 B2
(45) Date of Patent: Apr. 14, 2026

(54) ELECTROMAGNETIC RADIATION FOCUSING DEVICE AND APPLICATIONS THEREOF

(71) Applicant: GOYA DENTAL PTY LTD, West Gosford (AU)

(72) Inventor: Kyle Andrew Mervin, East Gosford (AU)

(73) Assignee: GOYA DENTAL PTY LTD, West Gosford (AU)

( * ) Notice: Subject to any disclaimer, the term of this patent is extended or adjusted under 35 U.S.C. 154(b) by 357 days.

(21) Appl. No.: 18/248,085

(22) PCT Filed: Sep. 15, 2021

(86) PCT No.: PCT/AU2021/051063
§ 371 (c)(1),
(2) Date: Apr. 6, 2023

(87) PCT Pub. No.: WO2022/077049
PCT Pub. Date: Apr. 21, 2022

(65) Prior Publication Data
US 2023/0411036 A1    Dec. 21, 2023

(30) Foreign Application Priority Data

Oct. 13, 2020    (AU) ................................. 2020903715

(51) Int. Cl.
*A61N 5/10*          (2006.01)
*G21K 1/02*          (2006.01)
(52) U.S. Cl.
CPC ........... *G21K 1/025* (2013.01); *A61N 5/1042* (2013.01); *A61N 2005/1095* (2013.01)

(58) Field of Classification Search
None
See application file for complete search history.

(56) References Cited

U.S. PATENT DOCUMENTS 2,638,554 A      5/1953  Bartow et al.
3,936,646 A *    2/1976  Jonker ................... G21K 1/025
                                                    976/DIG. 429

(Continued)

FOREIGN PATENT DOCUMENTS

WO      2015/152720 A2    10/2015

OTHER PUBLICATIONS

Extended European Search Report issued in European Patent Application No. 21878774.5, dated Aug. 13, 2024.

(Continued)

*Primary Examiner* — Hoon K Song
(74) *Attorney, Agent, or Firm* — Benesch Friedlander Coplan & Aronoff LLP

(57)          ABSTRACT

A focusing device for X-ray and Gamma-ray use in radiotherapy, the device comprising a radiopaque frustoconical shaped member having a first end and a second end, wherein the member comprises an array of radiolucent beam paths extending from the first end to the second end, wherein each of the beam paths has an entrance aperture at the first end, and an exit aperture at the second end; the entrance aperture through which source rays pass into the beam path, wherein the beam path emits a beam from the exit aperture when the source beams are in line with the longitudinal axis of the beam path or having a predetermined angle of deviation from the longitudinal axis of the beam paths; and wherein each of the longitudinal axis of the beam paths is angled relative to the longitudinal axis of the member for convergence towards a focal point or multiple points.

12 Claims, 6 Drawing Sheets

(56)                  References Cited

U.S. PATENT DOCUMENTS

| 4,348,591 | A   |   | 9/1982 | Wunderlich |
|---|---|---|---|---|
| 5,448,073 | A   |   | 9/1995 | Jeanguillaume |
| 5,627,870 | A   |   | 5/1997 | Kopecky |
| 6,185,278 | B1  | * | 2/2001 | Appleby ................ G21K 1/025 |
|   |   |   |   | 378/149 |
| 2010/0061511 | A1 |   | 3/2010 | Heid |
| 2013/0064350 | A1 |   | 3/2013 | Kerjean |

OTHER PUBLICATIONS

International Search Report and Written Opinion issued in PCT Application No. PCT/AU2021/051063, mailing date Oct. 22, 2023.
Wilson, R. J., "Collimator Technology and Advancements", Journal of Nuclear Medicine Technology, Memphis, 1998, vol. 16, No. 4, p. 198-203, 201, fig. 6.

\* cited by examiner

ELECTROMAGNETIC RADIATION FOCUSING DEVICE AND APPLICATIONS THEREOF

TECHNICAL FIELD

The present invention relates to a device for focusing electromagnetic radiation using straight radiolucent tubes embedded in a radio-opaque matrix that are angled relative to each other such that each beam of radiation when exiting the radiolucent tubes converge to a focal point. More particularly, the present disclosure may relate to an X-ray focusing device for use in radiotherapy or a microwave focussing device for thermal ablation as an alternative or adjunct to radiotherapy.

BACKGROUND

Radiotherapy to treat primary or metastatic tumours relies on the relative susceptibility to a radiation exposure of the DNA in cells that are in the cell cycle (i.e. duplicating themselves as in mitosis, or dividing into gametes for use in reproduction as in meiosis), as compared with those that are not. In non-dividing cells the DNA is compacted within the cell nucleus, once the cell moves into the cell cycle, the DNA disperses within the cell cytoplasm, and then replicates, both increasing the amount of DNA present within the single cell, and the volume it occupies within a single cell.

Metastatic or primary tumour cells by definition are in a more or less constant state of self-replication, whereas the cells in normal healthy tissue are not. Within healthy tissue, stem cells replicate and produce cells which then populate the tissue and differentiate into specific cell types.

It is the susceptibility of the stem cells to radiation mediated DNA damage that is the most significant drawback to radiation therapy, as DNA damage to stem cells can either kill stem cells, or cause mutations that persist in the progeny of that cell line, and may in fact trigger new cancer cells.

A significant drawback to radiation therapy, is that when it is used to target primary or secondary metastatic tumours, it is often required to pass through healthy tissue and stem cells in order to attack tumour cells. This occurs between the source of the beams and the tumour, and also once it has passed through the tumour in the healthy tissue between the tumour and the point at which the beams exit the body.

The present invention is an attempt to use geometry, to target a focal 3-dimensional position within a 3-dimensional structure, such that the target region experiences a high dose of radiation whilst the dose to the surrounding tissues is minimized.

There are 2 probabilities to consider when determining the relative effectiveness of a radio-surgical treatment. 1. The probability that a therapeutic photon will interact with the DNA of a target cell, and 2. the probability that an interaction with a target cell will result in cell death.

The energy contained within each subtype of EM photon impacts on the probability that the DNA damage caused by an interaction with a therapeutic photon will result in cell death, and in this context, gamma radiation is preferred. As gamma rays have energy in excess of 1 MeV, compared with X-rays which have photons with energy less than 100 keV, the damage caused to the DNA via the interaction with the gamma ray photon is more likely than an interaction with an x-ray photon to kill the cell. This is true of both the target cells and the stem cells that lie within the path of the therapeutic beam.

The other probability, the likelihood that a photon from a therapeutic beam will interact with the DNA, is identical irrespective of the radiation sub-type. 1000 photons from a gamma source is equally as likely to interact as 1000 photons from an x-ray source.

The present invention is designed to increase the probability of a therapeutic beam hitting the target mass, whilst diminishing the likelihood of adverse interactions within the healthy tissue. It is proposed that a geometric filter can be used to focus beams from a from expansive origins, such that the target tissue is exposed to a high number of damaging photons, while the surrounding healthy tissue experiences relatively few.

Additionally, by increasing the probability of a fatal interaction with the target tissue, (by increasing the number of photons incident upon the convergence focal point), it is proposed that effective treatment can be achieved with lower energy photons, thereby reducing the probability of fatal or damaging interaction with the healthy tissue.

Conventional treatments are achieved by directing the beam at the cancer cell or tumour cell from multiple directions by pointing multiple beams at the unhealthy cell. As the multiple beams are not parallel to each other, by this method, the point where the beams cross receives a higher dosage than the healthy tissue as the beam must pass through on the way. A possible disadvantage with this method may be that the beam intensity drops rapidly as it passes through the healthy tissue due to the Compton scattering by electrons in the tissue. As irradiation from many directions is required to achieve a good ratio of unhealthy cell to skin exposure, this technique is a problem. Further problems with Gamma rays include side scatter, over shooting and imprecision below a target size of about 5 mm By using an orthovoltage X-ray beam, the beam is cleaner, sharper and overshoots the target area less.

There are devices that can focus X-ray beams. An example is described in U.S. Pat. No. 6,560,312 which describes the focusing of X-rays using grazing incidence optics or other x-ray optical methods, in which the method uses spherical minors for such grazing incidence optics. Their system uses the reflection of incident X-rays with a polished surface at a sufficiently low angle. A possible disadvantage is that it may require more parts and minors to keep the incident beam at a low angle.

Other designs have been developed in the past to overcome the disadvantages mentioned above, however, most X-ray focusing optical systems have fixed optical parameters with constant numerical apertures. This lack of adaptability may have significantly limited application targets. In light of the aforementioned disadvantages, there exists a long-felt need to provide a device that may overcome one or more shortcomings of X-ray focusing devices as described in the prior art.

Many sources of higher energy radiation arise from a point source. This could be an x-ray generating tube where electrons are accelerated in an electrical field in a vacuum due to a high potential difference and smashed into a cathode, usually tungsten, which liberates large numbers of x-ray photons. Collimation is then usually applied to the exit point from the x-ray generating device and the photons emanating produce a diverging photon beam that is then used to pass through an object such as the human body with the photons that are not absorbed within the structure passing through to a detector or film on the opposing side of the object. Similarly, gamma rays may be produced by the nucleus of a radioactive element, known as a radionuclide or radioisotope, and these can be similarly contained in small point-like sources. In this case, the gamma photons are emitted in all directions equally in a 3D spherical geometry. Once they are emitted, the direction of these photons can only be shaped by removal of unwanted photons. The difficulty of construction of the high-density materials that are needed to absorb the unwanted photons (due to their very high energies) and let the remainder pass through. Conventional devices such as the nuclear medicine gamma camera and the multi-leaf collimator of the linear accelerator (LINAC) used in radiotherapy use lead or other high-density metals to restrict the photon beam from the required trajectory. The manufacturing processes around these materials are not simple and involve techniques such as casting molten lead, folding "crinkle cut" shaped lead foils into stacks, or drilling, all of which have significant limitations.

In medical imaging, lead collimators are found in the nuclear medicine gamma camera and similar devices. These typically have whole sizes limited to a minimum of 1 mm by the process of manufacturing. A gamma camera collimator of 50×40 cm may contain 50,000 to 80,000 such holes. Various grids and screens are used with lower energy X-rays but these are primarily aimed at scattered photon reduction to improve contrast in the image. In radiotherapy, the megavoltage (MV) x-ray photons that are produced by the linear accelerator are shaped by a large number (~128-256) of "finger-like" lead blocks in what is known as a multi-leaf collimator (MLC) that move rapidly in and out of the beam field driven by motors to constantly shape the beam to conform to the prescription defined in the software by the treating radiotherapist. With such a device, the shape of the radiation being delivered from many angles about the subject can be varied in real-time to give the desired pattern of energy deposition. However, the high-energy radiation still has to traverse the normal tissues around the abnormality and thus an amount of radiation impacts on normal tissues, which is also known as collateral damage. Much of the design of personalized radiotherapy treatments is a trade-off between minimising this normal tissue irradiation against delivering the maximum dose to the target area of interest. There is a long felt need to use a device that may well be in its ability to use much finer beams which are moved around during a treatment whilst remaining focused on the target which could significantly reduce the amount of irradiation of non-target tissues.

Other devices such as Gamma Knife, where a large number (~200) of individual radioactive sources of cobalt-60 ($^{60}$Co) are focused on a single point in the patient being treated to deliver a high dose of therapeutic radiation at the location defined. This Gamma Knife may be well evaluated clinically but is based on a large number of radiative sources, which is not a simple approach.

Any discussion of the prior art throughout the specification should in no way be considered as an admission that such prior art is widely known or forms part of common general knowledge in the field.

SUMMARY

Problems to be Solved

It may be an advantage to provide a device that selectively removes non-convergent therapeutic photons from a therapeutic electromagnetic radiation beam (or beams) for use in radiotherapy.

It may be an advantage to provide a radiopaque frusto-conical shaped member with an array of radiolucent beam paths in which each of the longitudinal axis of the beams paths is angled relative to the longitudinal axis of the member for convergence towards a focal point.

It may be an advantage to provide an array of apertures that have an entrance aperture that is staggered or offset relative to the adjacent entrance aperture so that when the device is spun, the convergent beams will pass through the surrounding tissues more evenly on its path to the focal target tissue, therefore traversing a greater volume of healthy tissue, but at a lower incident dose whilst maintaining the therapeutic dose on the focal target. This will look like a spiral pattern of apertures in a cross section 90° to the of the long axis of the device.

It may be an advantage to direct therapeutic beams in such a way to avoid the direct exposure of radiation to dividing cells in healthy regenerative tissue. Such as, in ovaries, reproductive organs, thyroid or other organs or glands.

It may be an advantage to provide an array of opaque tubes to ensure structural support of the frustoconical member.

It may be an advantage to provide a small width for the entrance aperture and a long length for the beam path for the device so that beams that can traverse entirely through the beam path have a lower predetermined angle range of deviation.

It may be an advantage to have numerous spatially separated x-ray (or other EM radiation) sources, and/or to have a scatter medium between the x-ray source (or sources) and the invention, to feed a sufficient quantum of x-rays to the focal target.

It may be an advantage to selectively choose photons travelling in a particular trajectory to either produce a focused beam of radiation. It does so using a two-stage process: firstly, a scattering medium is introduced between the photon source and the device and then, secondly, this is followed by the device, a more conventional physical collimator made of a high density material that is manipulated in certain motion patterns as required to produce the type of radiation trajectories for the particulate application.

The advantageous combination of the scattering medium that will cause the random changes in trajectory of photons emitted from the source and then the selectivity of the collimator to only allow those photons passing in the required direction to proceed through the non-absorbing channels of the device.

It may be an advantage to use a technique that has been adopted for this invention by using an electrical-based technique known as EDM (Electrical Discharge Machining) which relies on the material to be machined having electrical conduction properties with which accurate machining can be achieved to the level of a micron or so.

It may be an advantage for the device to rely on there being an abundant flux of photons available so that the ones that will be chosen to be directed from the device are of sufficient number to be able to effect the result desired, whether that be high spatial resolution imaging or delivering targeted and focused treatments.

It is an object of the present invention to overcome or ameliorate at least one of the disadvantages of the prior art, or to provide a useful alternative or adjunct.

Means for Solving the Problem

A first aspect of the present invention may relate to A focusing device for X-ray and Gamma-ray use in radiotherapy, the device comprising: a radiopaque frustoconical shaped member having a first end and a second end, wherein the member comprises an array of radiolucent beam paths extending from the first end to the second end, wherein each of the beam paths has an entrance aperture at the first end, and an exit aperture at the second end; the entrance aperture through which source X-rays or gamma rays pass into the beam path, wherein the beam path emits an X-ray or gamma ray beam from the exit aperture when the source X-ray or gamma ray beams are in line with the longitudinal axis of the beam path or having a predetermined angle of deviation from the longitudinal axis of the beam paths; and wherein each of the longitudinal axis of the beam paths is angled relative to the longitudinal axis of the member for convergence towards a single focal point or multiple focal points, wherein the focal point or points are distal from the device and extends to a point beyond the second end.

Preferably, the array of radiolucent beam paths is an array of radiolucent tubes, wherein each of the tubes defines a lumen for providing the beam path, and wherein the radiolucent tubes are embedded in the frustoconical member.

Preferably the cross-sectional shape of the radiolucent tubes may be at least one selected from the group of: square, circular, ovoid, diamond, slits, and triangles.

Preferably, the entrance aperture is staggered relative to an adjacent entrance aperture.

Preferably, the distance between the entrance aperture and an adjacent entrance aperture is greater than the distance between the exit aperture and an adjacent exit aperture.

Preferably, a first frustoconical member has a length longer than a second frustoconical member, the distance between the entrance aperture and the adjacent entrance aperture of the first frustoconical member is smaller than the distance between the entrance aperture and the adjacent entrance aperture of the second frustoconical member.

Preferably, the first frustoconical member has a length longer than the second frustoconical member, the width of the entrance aperture of the first frustoconical member is smaller than the width of the entrance aperture of the second frustoconical member.

Preferably, the predetermined angle of deviation from each of the longitudinal axis of the beam paths is less than 10°.

Preferably, the predetermined angle of deviation from the longitudinal axis of the tubes is less than 1°.

Preferably, the predetermined angle of deviation from the longitudinal axis of the tubes is 0°.

Preferably, the material of the frustoconical member is one selected from the group of: aluminium, zirconia, titanium, lead, tungsten, tungsten composite alloys, heavy metal alloys, tantalum, molybdenum, gold alloys, depleted uranium, and mercury amalgams.

Preferably, the frustoconical member comprises a central tube extending from the first end to the second end along the longitudinal axis of the member, wherein torque applied to the central tube allows for the rotation of the member.

Preferably, the slanted height of the frustoconical shaped member is 200 mm.

Preferably, the sector angle is between 20° and 160°.

Preferably, the surface of the device at the end where the x-rays enter is spherical.

Preferably, an apparatus adapted for use with the device, the apparatus comprising: a primary X-ray or gamma ray source or numerous spatially separated sources configured to radiate X-rays or gamma rays; a secondary x-ray source comprising a material that interacts with the x-rays or gamma rays produced by the primary sources, and produces through scatter interactions a secondary source of x-rays configured to feed x-rays into the device from a broad 3 dimensional field; the device positioned between the primary X-ray or gamma ray sources, and/or a secondary x-ray source, and a subject, wherein the first end of the frustoconical member is proximal to the radiation source and wherein the device is configured to focus the X-ray or gamma ray beams to the focal point or points, wherein the focal point or points are directed to a single predetermined zone or multiple predetermined zones of the subject.

In the context of the present invention, the words "comprise", "comprising" and the like are to be construed in their inclusive, as opposed to their exclusive, sense, that is in the sense of "including, but not limited to".

The invention is to be interpreted with reference to the at least one of the technical problems described or affiliated with the background art. The present aims to solve or ameliorate at least one of the technical problems and this may result in one or more advantageous effects as defined by this specification and described in detail with reference to the preferred embodiments of the present invention.

BRIEF DESCRIPTION OF THE FIGURES

FIG. 5 illustrates a beam path of a certain length with a scatter medium (or secondary source of therapeutic photons) before the entrance aperture of the device. The allowable angle of deviation from the longitudinal axis of the beam path is evident as the divergent lines emerging at point 24.

FIG. 6 illustrates the impact of increasing the aperture of the radiolucent tube but maintaining the same length as compared to FIG. 5. At a constant length, the greater the aperture, the wider the divergence of the emergent beam.

FIG. 7 illustrates the impact of the increasing the length of the device but maintaining the same aperture size when compared to FIG. 6. At a constant aperture size, the longer the device, the lower divergence of the permitted beam.

DESCRIPTION OF THE INVENTION

Preferred embodiments of the invention will now be described with reference to the accompanying drawings and non-limiting examples.

The overarching principle of the device is to maximize the therapeutic dose of radiation to the target tissue, whilst minimizing the exposure of the surrounding healthy tissue to potentially harmful radiation. As such the size of individual radiolucent paths can vary in cross sectional area, cross sectional shape, and longitudinal length. Additionally, the array of the radiolucent pathways within the device may be varied for specific therapeutic applications, or pragmatic manufacturing limitations.

Figure 1:
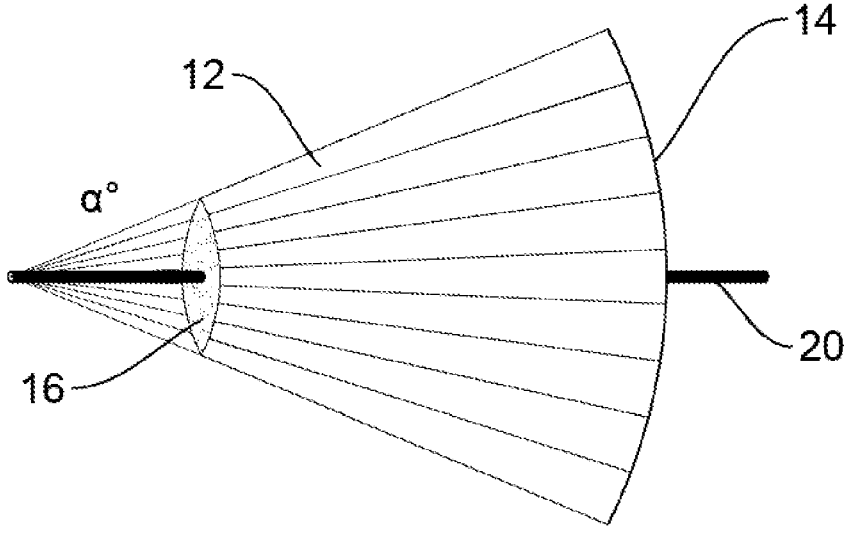
FIG. 1 illustrates a side view of the frustoconical shaped device with the central rod or spindle, whilst showing the convergent beam paths as the beams exit the exit aperture at the truncated end of the member.
Figure 2:
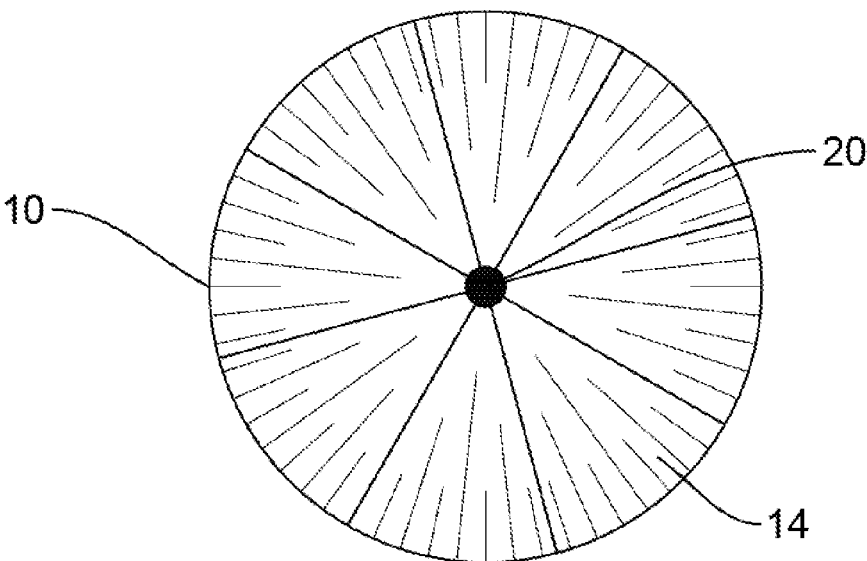
FIG. 2 illustrates the x-ray source end of the frustoconical shaped device with the central rod or spindle, with lines indicating the approximate location of entrance apertures.
Figure 3:
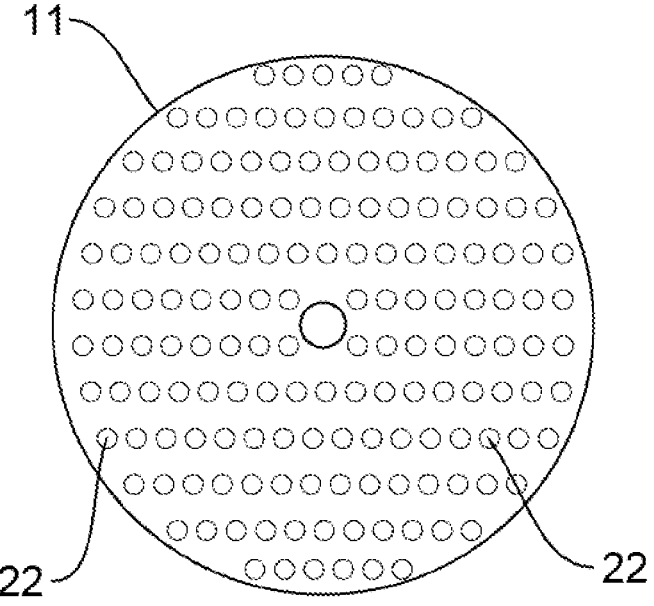
FIG. 3 illustrates a view of the x-ray source end of the frustoconical shaped device showing an example of a regular array of entrance apertures.
Figure 4:
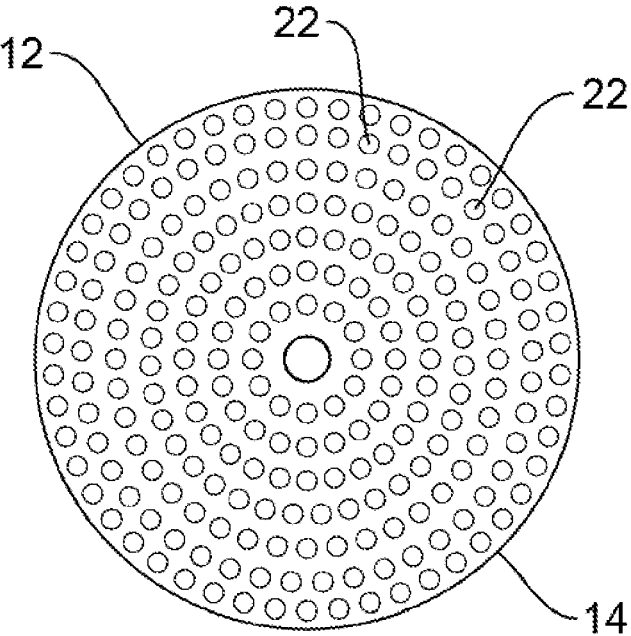
FIG. 4 illustrates a view of the x-ray source end of the frustoconical shaped device without the spindle and showing an array of entrance apertures with the entrance apertures in a set of concentric rings around the central rod or spindle.
Figure 10:
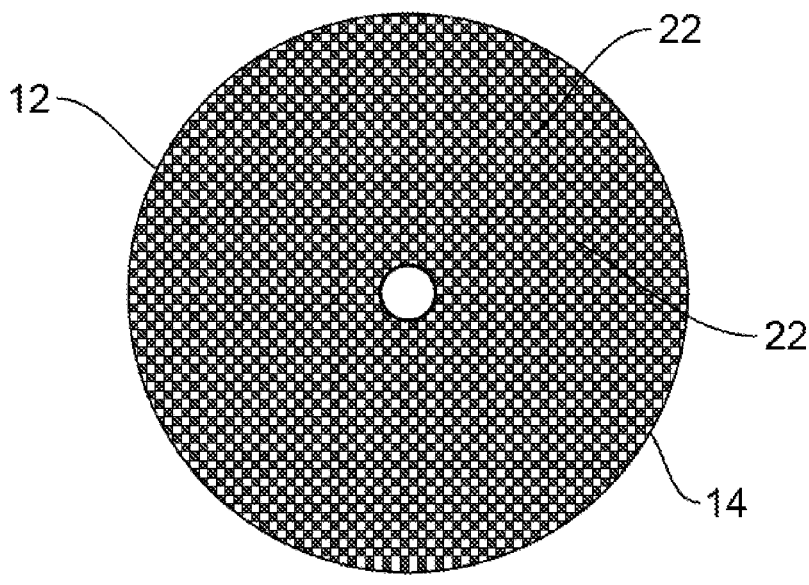
FIG. 10 illustrates a block filter cross-section schematic of a base or bottom view of the frustoconical shaped device without the spindle and showing the regular array of square entrance apertures.
Figure 11:
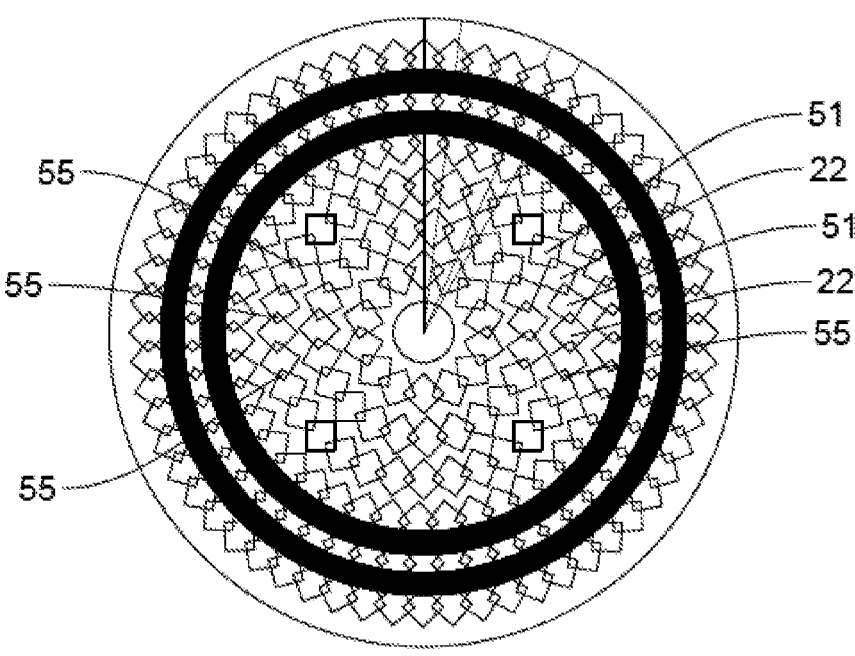
FIG. 11 illustrates a superimposition of lumens from blocks or segments that are offset relative to each other.

In an embodiment of the present invention, as illustrated in FIG. 1, the device 10 may be a member 12 having a frustoconical shape. The member 12 or matrix 12 may be radiopaque. The frustoconical shaped member 12 may have a first end 14 and a second end 16. The first end 14 may also be the base end 14 of the member 12, and the second end 16 may also be the truncated end 16 of the member 12. As shown in FIGS. 2, the base end 14 may have centre aperture 18, in which the centre aperture 18 is adapted receive a rod or spindle 20, in which the rod or spindle 20 is adapted to rotate the member 12 when torque is applied to the spindle 20. As shown in FIG. 3, the base end 14 may have an array of apertures 22. The array of apertures 22 may be in a regular pattern such that the aperture and the adjacent apertures have a constant regular pattern relative to each other but without a consistent radial relationship to the central spindle. In another embodiment of the present invention, as shown in FIG. 4, the array of apertures 22 may have a constant radial relationship to the spindle, appearing in concentric rings. As shown in FIGS. 3 and 4, the profile of each aperture may be a circle; or as shown in FIG. 10, the profile of each aperture may be a square or a rectangle; or as shown in FIG. 11, the profile of each aperture may be a diamond shape.

The cross sectional shape of individual radiolucent pathways may need to vary based on the type of EM radiation used, A specific example of this would be the used of slits to facilitate the passage of microwave radiation.

The array of apertures 22 from the base end 14 may be an array of entrance apertures 22, and the array of apertures 24 from the truncated end 16 may be an array of exit apertures 24. Between the entrance aperture 22 and the corresponding exit aperture 24 is a radiolucent beam path 26. The beam path 26 may be a straight path such that electromagnetic radiation, such as X-rays beams which are in line with the longitudinal axis of the beam path can enter the entrance aperture 22 and allowed to traverse through the entirety of the beam path of the member 12 and then emit the X-ray beam at the exit aperture 24.

Figure 5:
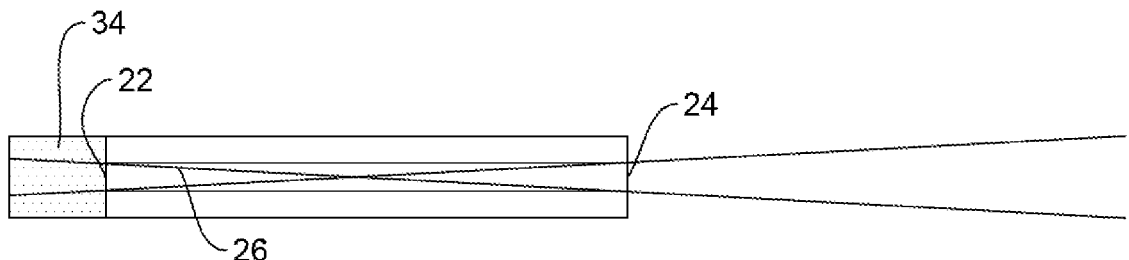
FIGS. 5, 6 and 7 illustrate the 2-dimensional impact of varying the cross-sectional area of the individual lumen (comparing FIGS. 5 and 6), or the length of the device (comparing FIGS. 6 and 7), on the permitted divergence of the emergent therapeutic beam (divergent lines beginning at 24. The area of the scatter medium (34) that contributes to the therapeutic beam is represented in each figure by the cross hatched trapezoid within 34.
Figure 6:
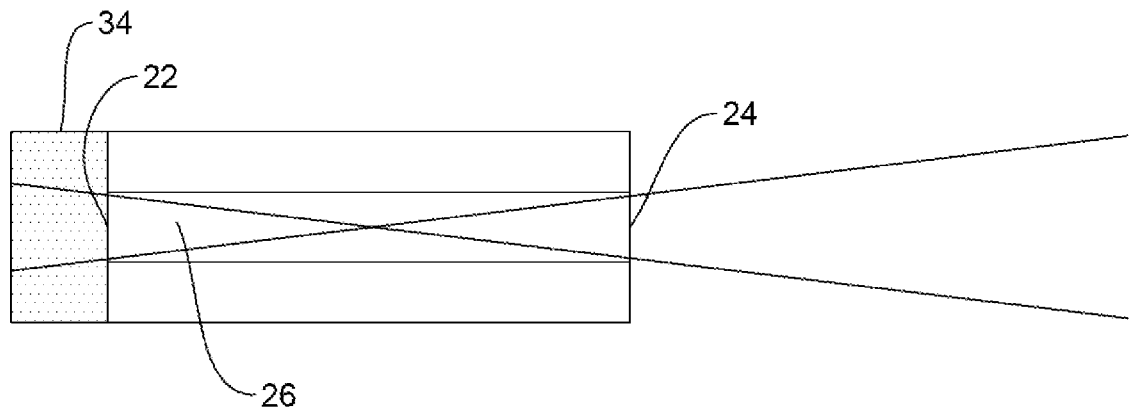
Figure 7:
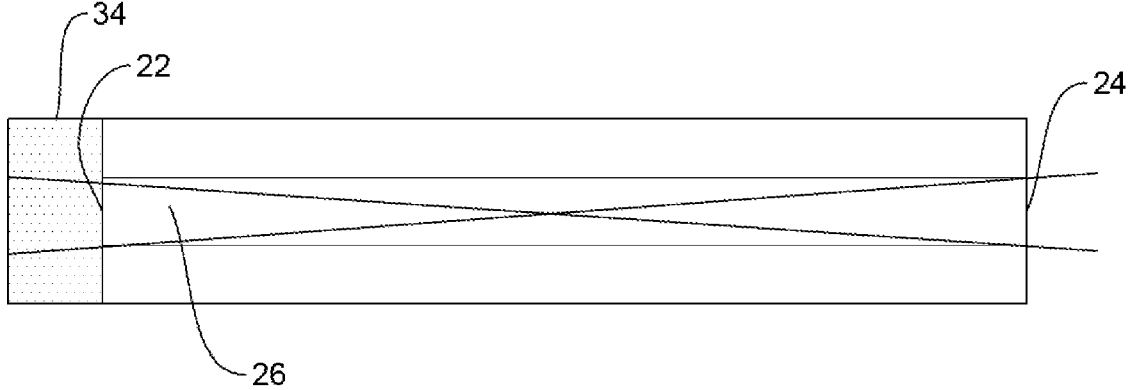

As shown in FIGS. 5, 6, and 7, while the X-ray beams which are in line with the longitudinal axis of the beam path are preferred, it may be appreciated that a small predetermined angle of deviation from the longitudinal axis of the beam paths can also enter the entrance aperture 22 and also allowed to traverse through the entirety of the beam path of the member 12 and then emit the X-ray beam at the exit aperture 24. Comparing the width of the beam paths 28 of FIGS. 5 and 6, the beam path 26 of FIG. 5 has a smaller width than the beam path of FIG. 6. As such, the predetermined angles allowable for source X-rays to traverse the length of the beam path 30 is relatively smaller than the predetermined angles allowed for a larger width of the beam path 26. Further, comparing the length of the beam paths of FIGS. 6 and 7, the beam path of FIG. 7 is longer than the beam path of FIG. 6. As such, the predetermined angles allowable for source X-rays to traverse the length of the beam path 26 is relatively smaller than the predetermined angles allowed for a shorter beam path 26. It may be appreciated that a smaller width and a longer beam path may be preferred so that the X-rays that are allowed to be emitted at the exit aperture are as close to line with the longitudinal axis of the beam paths as possible.

Figure 8:
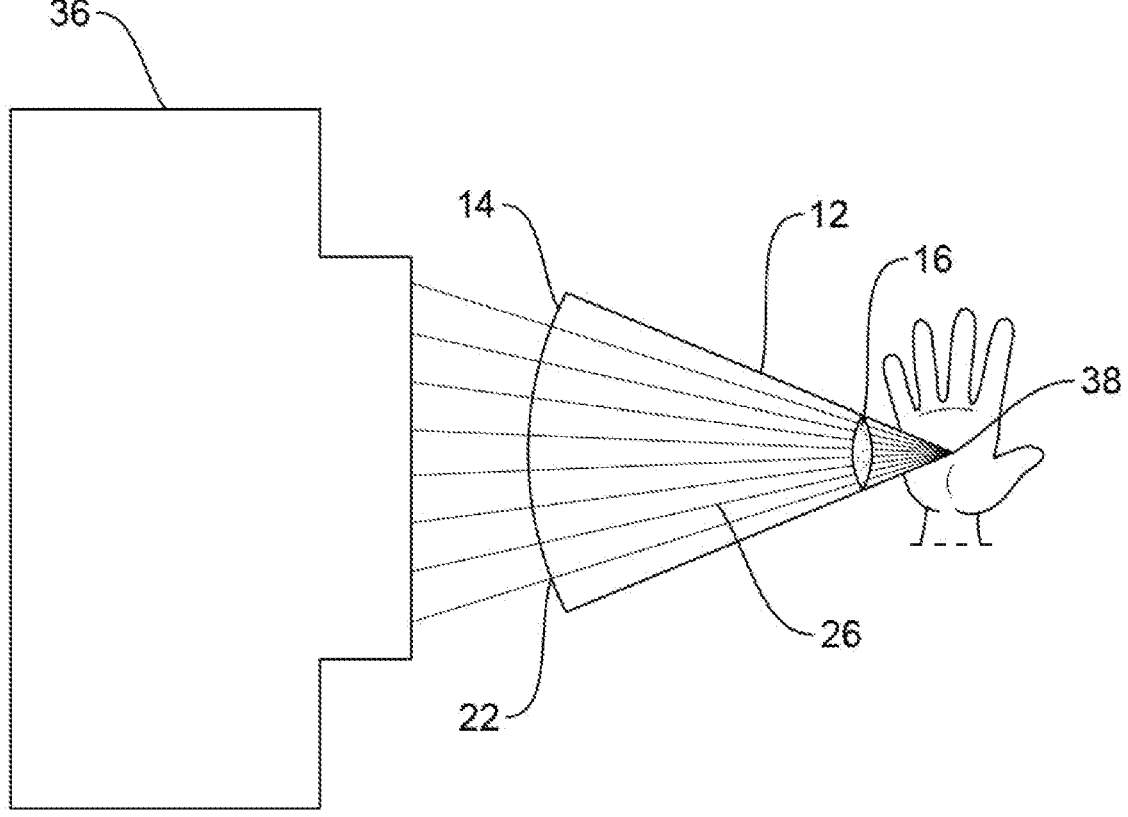
FIG. 8 illustrates a simple schematic of an electromagnetic radiation emitting apparatus in use with the frustoconical device for focusing the converging electromagnetic radiation towards the region of interest of a subject.

As shown in FIGS. 1 and 8, each of the longitudinal axis of the beam paths 26 may be angled relative to the longitudinal axis of the member 12 for convergence towards a focal point 32. The focal point 32 may be distal from the device 10 and extends to a point beyond the second end or the truncated end 16 of the member 12. For example, in use wherein the device 10 is used with an X-ray generator 32, the source X-ray beams may exit the X-ray generator 32 in different directions. While the source X-rays may be in different directions, only the source X-rays beams that are either in line with the longitudinal axis of the beam paths or within the predetermined angle of deviation will selectively traverse the entire path of the beam path 26. When the source X-ray beams are entering the entrance aperture 22 at an angle that is greater than the predetermined angle of deviation, the X-ray beam will enter partially into the beam path 26 before encountering the radiopaque material that defines the beam path 26. As such, that source X-ray beam will not be able to emit from the exit aperture 24.

It may be appreciated that the device may be constructed from aluminium, zirconia, titanium, or lead or any particulate matter that may be radiopaque with beam paths 26 from an array of entrance apertures 22 to the array of exit apertures 24. It may also be appreciated that the device may also be constructed from Tungsten or heavy metal composites or alloys. For example, materials for its construction may include one selected from the group of: Tungsten/copper alloy composites, Molybdenum, Tantalum, gold alloys, depleted uranium, and mercury amalgams. The radiopaque particulate matter may be chosen that can be bound in a resin for 3-dimensional printing or production purposes. Preferably, for strengthening the structural support of the member 12, the array of radiolucent beam paths 26 may be an array of radiolucent tubes, in which each of the tubes may define a lumen 26 for providing the beam path 26. The radiolucent tubes may be embedded in the frustoconical member 12 or matrix 12.

It should be noted that a radiolucent path must be radiolucent for the entire length of the device, but the radiopaque material or matrix is not required to traverse the entire length (although it would be preferred). The device will adequately block divergent photons provided there is a sufficient length of radio-opaque material lining the lumen at the entrance and exit apertures, and the void in between those points is not likely to significantly contribute scattered radiation to the emergent beam. This may provide a significant weight advantage in the practical application of the device, and manufacturing.

While the device or collimator 10 may be formed by metal extrusion, it may be appreciated that the device or collimator 10 may be manufactured by materials such as an aluminium alloy which may be suitable for 3D-printing. For example, the aluminium alloy used may be AlSi7Mg0.6. Advantages of manufacturing the device 10 via 3D printing may be rapid prototyping and cost-effective manufacturing. The 3D-printed device 10 may be joined by a series of layers or blocks/segments in a linear configuration to form the frustoconical shape. The first block/segment may have a first end 50 and a second end 52 and the second block/segment may have a first end 54 and a second end 56. The second end 52 of first block/segment may be joined to the first end 54 of the second block/segment and the second end 56 of the second block/segment may be joined to the first end of a third block/segment, in which the third block/segment may be the same as the first block/segment. Similarly, the fourth block/segment may be the same as the second block/segment. The block/segment may also be termed as a layer.

The first end 50 of the first block/segment or an odd number block/segment in the series may have an array of diamond shaped entrance apertures 22, and the first end 54 of the second block/segment or an even number block/segment in the series may have an array of diamond shaped entrance apertures 51. Similarly, the second end 52 of the first block/segment or an odd number block/segment in the series may have an array of diamond shaped exit apertures 24, and the second end 56 of the second block/segment or an even number block/segment in the series may have an array of diamond shaped exit apertures 59.

Figure 12:
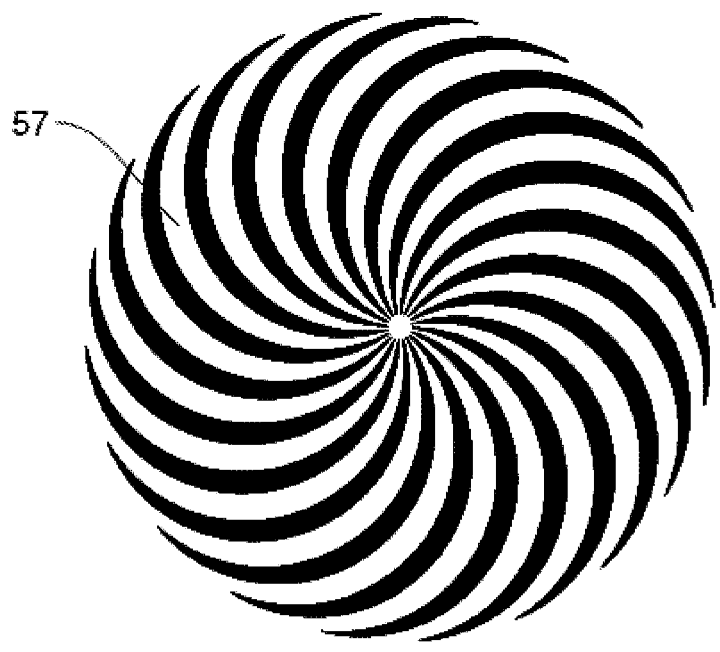
FIG. 12 illustrates the projection of the rotation of the device with the superimposition of lumens from FIG. 11.

As shown in FIG. 11, the first layer may have a first array of apertures 22 that may have a diamond profile shape. The second layer may have a second array of apertures 51 that may have the same diamond profile shape as the first layer however, the second layer or the subsequent layer may be offset from the first layer such that a right corner of the diamond aperture of the first layer is overlapping or intersecting with a left corner of the second layer thereby forming a smaller diamond shaped aperture 55 for the beam path 26. The third layer with similar apertures as the first layer may be relatively behind the first layer and may be offset to the second layer. Similarly, the fourth layer with similar apertures as the second layer may be relatively behind the second layer and may be offset to the third or previous layer. It may be appreciated that there may be any number of even numbered layers and odd numbered layers to stacked to form the elongate housing as long as the even numbered layers may be relatively offset to the odd numbered layers. This method of manufacture may provide the advantage of refining the size of the beam path, without requiring smaller tubes whilst also overcoming a problem with the curing process of 3D printers, in which the printed 200 nm tubes may be partially collapsing during the curing process. The first block or segment may have a first array of diamond apertures and the overlaying second block or segment may have a second array of diamond apertures offset from the first array of diamond apertures. As shown in FIG. 11, the superimposition of lumen in blocks may have an aperture size smaller than the apertures of the first array or the second array. When the elongate housing having the superimposition of lumen as illustrated in FIG. 11 is rotated, the emitted electromagnetic radiation may have a spiral pattern 57 as illustrated in FIG. 12.

As shown in FIG. 3, the entrance apertures 22 may be in a regular array of apertures wherein the aperture is equidistant to the adjacent apertures. More entrance apertures 22 in the array may allow more source X-rays that are in line with the longitudinal axis of the beam paths to converge to a focal point to provide a localised orthovoltage X-ray beam to the desired subject region. As shown in FIG. 4, the entrance apertures 22 may be in an irregular pattern or in a staggered or offset configuration. When torque is applied to the spindle 20, the member 12 may rotate and the convergent X-ray beams may create a spiralling circle pattern that may be random and independent from the other beam paths. The X-ray beams may spirally converge to the focal point, which may be advantageous to provide overlapping convergent X-ray beams so that better coverage can be attained for the target area of the subject region.

Figure 9:
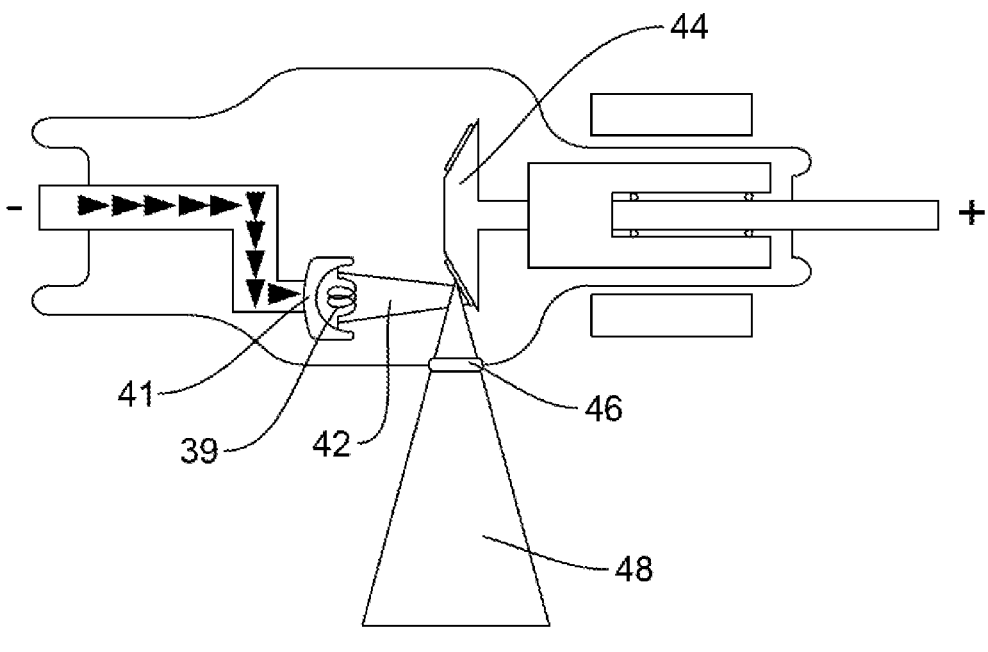
FIG. 9 illustrates a conventional schematic of an X-ray tube showing the parts and the X-ray photon beam emitted from the window of the X-ray tube.

As shown in FIGS. 8 and 9, there may be an X-ray tube 36 which is a vacuum tube that converts electrical input power into X-rays. As with any x-ray tube, there is a voltage gradient between a filament or cathode 39 which becomes the electron source, and the anode 44, which receives the electrons. The voltage gradient causes the electrons to jump across the vacuum with high energy (42) and strike the anode (usually spinning) which then converts the energy of the electrons into x-ray radiation. X-rays are emitted from the anode in all directions on a radial trajectory from their point of origin in the anode (44), The radio-opaque construction of the tube blocks the x-rays from escaping in all directions, but provides a window (46) through which x-rays escape and form the useful beam.

A high voltage power source may be used, for example 30 to 150 kilovolts (kV), or the tube voltage, may be connected across the cathode 39 and anode 44 to accelerate the electrons. The X-ray spectrum emitted depends on the anode material and the accelerating voltage. Electrons from the cathode may collide with the anode material, which may be chosen from tungsten or molybdenum or copper. The range of photonic energies emitted by this X-ray tube can be adjusted by changing the applied voltage and the use of aluminium filters of varying thicknesses. Aluminium filters may be installed in the path of the X-ray beam to remove low energy radiation. The number of emitted X-ray photons, or dose, is adjusted by controlling the current flow and exposure time.

Other variations of this simple design, such as a rotating anode tube may be used to generate X-rays for this invention. With higher voltage gradients, electrons generated strike the anode with higher energy, which generates higher energy x-rays but also cause heat to build up on the focal spot of the anode. By rotating the anode, the electron beam sweeps a larger area of the anode dissipating the resultant heat over a greater area and allowing for the production higher intensity wavelengths of emitted radiation, without the risk of heat damaging the apparatus. Typical anodes are a tungsten-rhenium target on a molybdenum core, backed with graphite. The rhenium makes the tungsten more ductile and resistant to wear from the impact of the electron beams. The molybdenum conducts heat from the target whilst the graphite provides thermal storage for the anode and reduces its mass.

There may be an X-ray focal spot within the X-ray tube 36 that may produce X-rays in a spherical manner. The X-ray focal spot may be a primary source of X-rays for this system. A cone of primary X-rays may emanate from the X-ray focal spot which may strike the scatter medium 34, which is positioned between the X-ray generator 32 and the base end 14 of the member 12. The scatter medium 34 may interact with the x-rays from the primary sources, which then becomes a secondary source of X-rays with a far greater surface volume, which then emit X-rays in a random spherical manner. The X-rays then strike the device 10, in which any of the X-ray beams that cannot travel entirely through the beam path are filtered away. As such, this device 10 selectively allows for converging X-ray beams that are concentrated to a focal point 32, which may be used to direct the convergent X-ray beams to the desired subject region 38 which may be subject to radiation therapy or radiotherapy.

This type of therapy uses ionising radiation, generally as part of cancer treatment to control or kill malignant cells. Radiation therapy may be curative in a number of types of cancer if they are localised to one area of the body. Radiation therapy is commonly applied to the cancerous tumour because of its ability to control cell growth. Ionising radiation works by damaging the DNA of cancerous tissue leading to cellular death. To minimise the exposure of the X-ray beams to the normal tissues, shaped radiation beams are aimed at the tumour thereby providing a much larger absorbed dose at that region than in the surrounding healthy tissue.

It may be appreciated that there are a number of ways to generate high energy photons as a primary source, including radioactive sources such as cobalt-60 that generate gamma radiation 32 to feed the present invention with or without a secondary scatter medium 34.

It may be appreciated that different sized frustoconical shaped members 12 or matrix 12 and size of the apertures may be used depending on the purpose. It may also be appreciated that this device 10 may be used with other electromagnetic radiation, such as UV-C radiation or microwave radiation for radiotherapy, when either UV-C radiation or microwave radiation therapy is more suitable for the application. The same principle applies where the device 10 may be placed in the same manner between the UV lamp or microwave generator and the desired subject region, similar to the illustration of FIG. 8 such that the UVC or microwave beams converge to the focal point 32.

For the frustoconical shaped member 12, the cross-sectional area of the base end 14 may be greater than the cross-sectional area of the truncated end 16. As such, the distance between the entrance aperture 22 and an adjacent entrance aperture 22 may be greater than the distance between the exit aperture 24 and an adjacent exit aperture 24 of the same member 12. When there are different sized frustoconical shaped members 12a and 12b, a first frustoconical member 12a may have a length longer than a second frustoconical member 12b. The distance between the entrance aperture 22a and the adjacent entrance aperture 22a of the first frustoconical member 12a may be smaller than the distance between the entrance aperture 22b and the adjacent entrance aperture 22b of the second frustoconical member 12b. The first frustoconical member 12a may have a length longer than the second frustoconical member 12b, wherein the width of the entrance aperture 22a of the first frustoconical member 12a is smaller than the width of the entrance aperture 22b of the second frustoconical member 12b.

Preferably, the beam paths may have a width and length that allows for a small predetermined angle of deviation from each of the longitudinal axis of the beam paths 26. The range of the predetermined angle may be less than 10°. Desirably, the range of the predetermined angle may be less than 1°. Most desirably, the predetermined angle of deviation from the longitudinal axis of the beam paths or radiopaque tubes is 0° or in line with the longitudinal axis of the beam paths 26.

The device is constructed from materials such as aluminium or lead (or titanium etc) with a certain thickness so that X-rays beams cannot penetrate out of the device 10 that are beyond the acceptable angle of deviation ranges with respect to the beam path. It may be appreciated that the member 12 may have a slant height that varies based on the application, and the desired distance from the focal target. Preferably, the slant height is 200 mm. It may be appreciated that the slant height may be as long as can be accommodated within practical limits and specific requirements. As shown in FIG. 1, it may be desirable to have the sector angle, α°, to range between 20 and 160°.

In another embodiment of the present invention, another application of the device may be a part used in a 3D printer or the device 10 may be incorporated into a 3D printer to print materials. As illustrated in FIG. 1, as the device 10 has a focal point, the high energy radiation can be focussed to a point by use of the device 10. The focussed high energy radiation can create an intense heat to sinter materials within a powder cartridge. The intense heat focussing on a position within a 3D space may confer the advantage of allowing printing in 3D without the need for layering or moving the cartridge, or alternatively moving the cartridge in 3 dimensions as opposed to the current systems that may move the cartridge in 2 dimensions per layer, and then moves the cartridge 50 nm to print the next layer.

In another embodiment of the present invention, another application of the device 10 may be a part used in welding, to supply heat to metals or other structural materials both on the surface of a structure and or at depths within existing 3 dimensional objects. The focussed high energy radiation can create an intense heat to melt metals or other materials such that the metals or other materials from adjacent structures melt and flow together and combine to form bonds typical of welded surfaces upon cooling.

In another embodiment of the present invention, another application of the device may be a part used in subtractive engineering, to supply heat to metals or other structural materials both on the surface of a structure and or at depths within existing 3 dimensional objects. The focussed high energy radiation can create an intense heat to melt metals or other materials with high precision and accuracy, such that the metals or other materials may be cut away from existing structures comparable with computer numerical control machining.

Although the invention has been described with reference to specific examples, it will be appreciated by those skilled in the art that the invention may be embodied in many other forms, in keeping with the broad principles and the spirit of the invention described herein.

The present invention and the described preferred embodiments specifically include at least one feature that is industrial applicable.

The invention claimed is:

1. A focusing device for X-ray or Gamma-ray use in radiotherapy, the device comprising:

a radiopaque frustoconical shaped member having a first end and a second end, wherein the radiopaque frustoconical shaped member comprises:

a first layer positioned adjacent a second layer along a longitudinal axis of the radiopaque frustoconical shaped member, the first layer having a first array of apertures, and the second layer having a second array of apertures; the second layer positioned between the first layer and the second end; such that a pair of adjacent apertures from the second layer each partially overlaps with a respective aperture of the first layer; and an array of radiolucent beam paths extending from the first end, through the first layer and the second layer, to the second end, wherein each of the radiolucent beam paths has an entrance aperture at the first end, and an exit aperture at the second end, wherein source X-rays or gamma rays pass through the entrance aperture into the radiolucent beam path, and the radiolucent beam path emits an X-ray or gamma ray beam from the exit aperture when the source X-ray or gamma ray beams are in line with the longitudinal axis of the radiolucent beam path or have a predetermined angle of deviation from the longitudinal axis of the radiolucent beam paths; and wherein each of the longitudinal axis of the radiolucent beam paths is angled relative to the longitudinal axis of the radiopaque frustoconical shaped member for convergence towards a single focal point or multiple focal points, wherein the focal point or points are distal from the device and extends to a point beyond the second end.

2. The device according to claim 1, wherein the array of radiolucent beam paths is an array of radiolucent tubes, wherein each of the tubes defines a lumen for providing the radiolucent beam path, and wherein the radiolucent tubes are embedded in the radiopaque frustoconical shaped member.

3. The device according to claim 1, wherein the entrance aperture is staggered relative to an adjacent entrance aperture.

4. The device according to claim 1, wherein the distance between the entrance aperture and an adjacent entrance aperture is greater than the distance between the exit aperture and an adjacent exit aperture.

5. The device according to claim 1, wherein the predetermined angle of deviation from the longitudinal axis of the radiolucent beam paths is less than 10°.

6. The device according to claim 5, wherein the predetermined angle of deviation from the longitudinal axis of the radiolucent beam paths is less than 1°.

7. The device according to claim 5, wherein the predetermined angle of deviation from the longitudinal axis of the radiolucent beam paths is 0°.

8. The device according to claim 1, wherein the material of the radiopaque frustoconical shaped member is one selected from the group of: aluminium, zirconia, titanium, lead, tungsten, tungsten composite alloys, heavy metal alloys, tantalum, molybdenum, gold alloys, depleted uranium, and mercury amalgams.

9. The device according to claim 1, wherein the radiopaque frustoconical shaped member comprises a central tube extending from the first end to the second end along the longitudinal axis of the radiopaque frustoconical shaped member, wherein torque applied to the central tube allows for the rotation of the radiopaque frustoconical shaped member.

10. The device according to claim 1, wherein a slanted height of the radiopaque frustoconical shaped member is 200 mm.

11. The device according to claim 10, wherein a sector angle of the radiopaque frustoconical shaped member is between 20° to 160°.

12. An apparatus adapted for use with the device of claim 1, the apparatus comprising:
a radiation source configured to radiate X-rays or gamma rays;
the device positioned between the radiation source and a subject, wherein the first end of the radiopaque frustoconical shaped member is proximal to the radiation source and wherein the device is configured to focus the X-ray or gamma ray beams to the focal point or points, wherein the focal point or points are directed to a single predetermined zone or multiple predetermined zones of the subject.

\* \* \* \* \*